United States Patent [19]
Nilson

[11] Patent Number: 4,664,257

[45] Date of Patent: May 12, 1987

[54] METHOD AND CAPSULE FOR STORING AND MIXING THE TWO CO-OPERATIVE BASIC MATERIALS OF DENTAL AMALGAM AND METHOD IN MANUFACTURING THE CAPSULE

[75] Inventor: Nils B. Nilson, Mjölby, Sweden

[73] Assignee: Kenova AB, Malmo, Sweden

[21] Appl. No.: 256,277

[22] Filed: Apr. 23, 1981

[30] Foreign Application Priority Data

Apr. 23, 1980 [SE] Sweden ............................... 8003067

[51] Int. Cl.⁴ ............................................ B65D 25/08

[52] U.S. Cl. .................................. 206/219; 206/63.5; 366/130; 366/602

[58] Field of Search .............. 206/219, 221, 277, 63.5, 206/438, 484, 526, 568, 220; 229/56, 65, DIG. 2, DIG. 4; 493/931, 209; 366/602, 130

[56] References Cited

U.S. PATENT DOCUMENTS

| | | | |
|---|---|---|---|
| 1,288,132 | 12/1918 | Nagle | 229/DIG. 4 |
| 2,876,602 | 3/1959 | Ditlea | 493/209 X |
| 2,917,631 | 12/1959 | Hyzer | 206/222 X |
| 3,087,606 | 4/1963 | Bollmeier et al. . | |
| 3,149,943 | 9/1964 | Amador | 206/484 |
| 3,275,302 | 9/1966 | Horton . | |
| 3,339,716 | 9/1967 | Taylor . | |
| 3,357,545 | 12/1967 | Kobernick . | |
| 3,451,540 | 6/1969 | Kulischenko . | |
| 3,478,871 | 4/1968 | Sager | 206/221 |
| 3,595,439 | 7/1971 | Newby et al. . | |
| 3,608,709 | 9/1971 | Pike | 206/219 |
| 3,625,349 | 12/1971 | Muhlbauer . | |
| 3,809,224 | 5/1974 | Greenwood | 229/56 |
| 4,023,675 | 5/1977 | Claasen . | |
| 4,306,651 | 12/1981 | Mühlbauer | 206/219 |

FOREIGN PATENT DOCUMENTS

| | | |
|---|---|---|
| 2831005 | 7/1976 | Fed. Rep. of Germany . |
| 1427933 | 1/1966 | France . |
| 7906465 | 7/1979 | Sweden . |

*Primary Examiner*—William Price
*Assistant Examiner*—Bryon Gehman
*Attorney, Agent, or Firm*—Finnegan, Henderson, Farabow, Garrett & Dunner

[57] ABSTRACT

The invention relates to a method and a capsule for the storage and mixing of the two co-reactive basic materials for dental amalgam. The capsule comprises an elastically bendable length of tube bent into V-shape with the arms each forming chambers and with the tip between the arms forming a point of separation between the chambers. Each of the basic materials is accommodated and stored in its own chamber and can be mixed by straightening out the length of tube, the ends of which are sealed, so that the point of separation is opened up, and by shaking the length of tube in its axial direction. The invention also relates to a method in manufacturing the capsule in which the tube length prior to bending into V-shape is pre-shaped in one section at the center of the length of the tube by providing two transverse points of compression which are mutually separated by an intervening section.

6 Claims, 8 Drawing Figures

13 14 11 12 17 10 18 15 10 B

10
FIG. 1
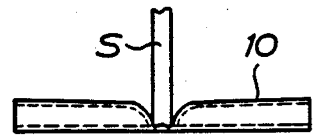
FIG. 2
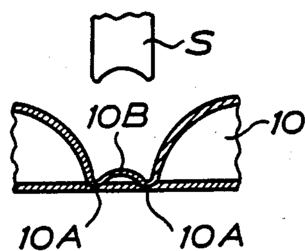
FIG. 3
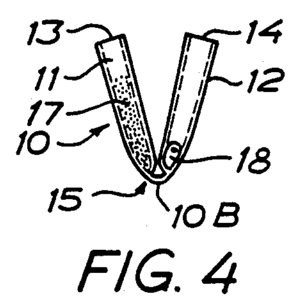
FIG. 4
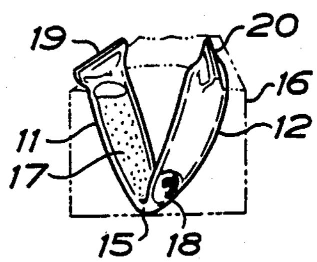
FIG. 5
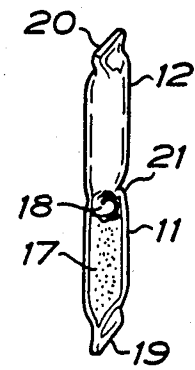
FIG. 6
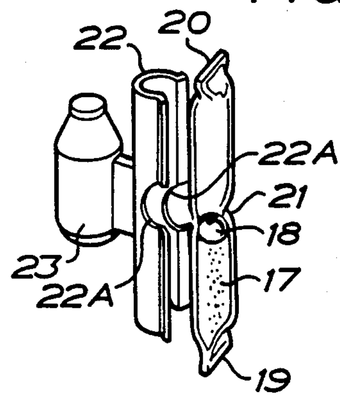
FIG. 7
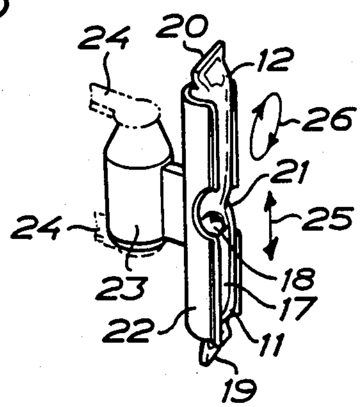
FIG. 8

METHOD AND CAPSULE FOR STORING AND MIXING THE TWO CO-OPERATIVE BASIC MATERIALS OF DENTAL AMALGAM AND METHOD IN MANUFACTURING THE CAPSULE

BACKGROUND OF THE INVENTION

The present invention relates to a method for storing and mixing two co-reactive basic materials for dental amalgam, usually a silver alloy (in a typical case containing—apart from silver—also tin, copper and zinc), known in the art as alloy, functioning as one component and pure mercury as the second component.

The invention also relates to a capsule for storing and mixing the two co-reactive components by employing the method in accordance with the invention, and furthermore relates to a method in manufacturing this capsule.

In the sphere of dentistry many proposals have been made for capsules for amalgam whereby quantities proportioned in advance of the two co-reactive components are stored in the capsule separate from each other and can be brought together and mixed directly in the capsule so as to react with each other whilst forming amalgam directly prior to its proposed use.

The capsules now available on the market include a chamber for each component with an openable point of separation between the chambers. Several different principles are employed to open the point of separation.

In one embodiment (U.S. Pat. No. 3,275,302) a ball or disc which rests on a seating between the chambers forms the point of separation between the chambers, the said separation being opened by shaking the capsule so as to mix the components with each other. The ball or disc at the same time forms a mixing body, known as a pistil, when the capsule is shaken during mixing. One significant disadvantage of this capsule consists in the fact that the capsule is sensitive as regards its position; it must not be turned upside down before mixing is to take place.

In another embodiment (U.S. Pat. No. 3,357,545) the capsule contains two portions which are adjustable relative to each other with an aperture between the chambers formed by the sections which can be opened and closed by turning or moving the sections relative to each other.

The method is also known (U.S. Pat. No. 3,625,349) wherein, in a capsule which consists of two rotatable components arranged excentrically relative to each other, mercury is provided in a small bag of plastic foil which is torn open by rotating the sections relative to each other so that the mercury can be pressed out of the bag through an aperture between the sections and into a chamber which contains the alloy.

Capsules having two sections which are telescopically displaceable mutually are also known wherein the sections are pressed telescopically together so that a membrane between the chambers which functions as the point of separation will by this means be broken, either because one section is pressed directly against the membrane (U.S. Pat. No. 3,451,540) or by one section pressing on the mercury which in turn presses against membrane (U.S. Pat. No. 3,595,439). The membrane can also be shaped like a small bag of plastic foil which contains the mercury and which rests loosely in a chamber which contains the alloy. The plastic bag is broken up in that the capsule sections are pressed telescopically together when the components are to be mixed with each other.

Apart from the fact that these known dental capsules are complicated in design, in certain cases extremely complicated, and hence relatively expensive to produce which is a distinct disadvantage, when—as here—they are to be throwaway capsules they suffer from the disadvantage that a particular manipulation of the capsule is required before the components can mix, and furthermore this is a manipulation which in some cases requires the exercise of quite a great deal of force. If the mercury is located in a small plastic bag inside the chamber for the alloy, there is furthermore the shortcoming that the plastic foil remains behind in the resultant amalgam in the form of one or more pieces and has to be separated out from the amalgam when this is removed from the capsule for use.

A dental capsule has been proposed which does not require any special manipulation before the mixing of the components (Swedish patent application No. 7906465-5). The capsule comprises a chamber for each of the components, and the chamber which contains the alloy also contains a rammer which when the capsule is shaken knocks repeatedly against a displaceable separating wall between the chambers. By this means the separating wall is pressed successively into the chamber containing the mercury, thus opening up passages which permit the mercury, during the movement of the separating wall, to be forced past the said wall into the chamber with the alloy. However this capsule is just about as complicated as the capsules described above and furthermore requires fairly high precision during manufacture.

One problem which has either not been considered at all or only inadequately in the case of the dental capsules described above is that mercury in extremely fine-particle form can penetrate outwards between the displaceable sections which are rotatable or telescopically displaceable relative to each other, or in the joints between the sections of the capsule which have to be separated in order to take out the finished amalgam. When mixing of the components takes place whilst the capsule is being shaken at high frequency, which is performed in special shaking devices available for the purpose, the mercury is flung out in the form of microscopically small droplets which have a very large cumulative surface and thereby a correspondingly high vaporisation rate. It is known that the daily respiration of air contaminated by mercury vapour can result in chronic mercury poisoning, and consequently the fact is not unknown that in dental surgeries there is some risk of such poisoning, even though the frequency of its occurrence is assumed to be low. This occupational hygiene health risk is hence probably slight, but even so having regard to its consequences, it is well worth taking into account when designing dental capsules particularly since mercury can cause damage also in other ways, namely by giving rise to allergic reactions in certain persons.

The problem of mercury leakage from dental capsules during shaking of the capsule in order to prepare the amalgam has been discussed in the literature and has also been subject to investigations and proposals have also emerged for a dental capsule which is designed to eliminate the risk of mercury escape. This dental capsule (German laid-open specification No. 28 31 005.6) is relatively simple in design. One chamber has a welded-on or glued-on cover with a breakage point, and in this chamber which contains the alloy, the other chamber is located in the form of a bag of thin plastic foil which encloses the mercury. When the capsule is shaken the bag is broken open against the end walls of the capsules and when the amalgam is ready the cover is broken away from the rest of the capsule at the breakage point using a special puncturing device. Apart from the fact that in this case too there is the disadvantage of encountering foreign substances in the amalgam, i.e. the disintegrated plastic bag which can be in the form of one or more pieces, the attachment of the cover whilst providing a breaking point after the capsule has been filled with the components does involve some complication, as does the breaking up of the cover which cannot be performed just as comfortably as when separating two components which are pushed together.

BRIEF SUMMARY OF THE INVENTION

The objective of the present invention is to make it possible to store and mix the two co-reactive components for dental amalgam whilst satisfying all the requirements which could be imposed namely:

Storage and mixing can occur in a capsule of simple design, so that the capsule can be produced at low cost and is thus quite suitable for throwaway use.

Filling of the capsule with the two components can be undertaken in a simple manner using an automated method.

The components can be kept separate in a reliable manner even during storage in the capsule for a long period.

The components can be merged together in the capsule by a simple manipulation of the capsule without any noteworthy amount of force being required.

Mixing can take place in the capsule by shaking it without risk of the material forcing its way out of the capsule; and mixing can take place without foreign objects coming into contact with the components or being mixed into the material.

This objective is achieved surprisingly simply by means of the method in accordance with the present invention for storing and mixing the two co-reactive basic materials for dental amalgam, which is characterised in that the basic materials are stored in a packaging, of a type known as such, consisting of an elastically flexible length of tubing bent into V-shape which is sealed at the ends and in which the fold between the arms forms a point of separation between the basic material accommodated in each arm of the length of tube, and in that the basic materials after straightening out the length of tube are mixed with each other by means of a shaking movement which has one component in the axial direction of the straightened tube length.

The capsule proposed for implementing this procedure is of a type which as such is previously known (U.S. Pat. No. 3,478,871), which has hitherto not been employed for storage and mixing of the two co-reactive basic materials for dental amalgam, and which consists of an elastically flexible length of tubing bent into V-shape with the arms sealed at the ends, each forming a chamber, and with the tip between the arms forming a separating point between the chambers, the said point of separation being openable by straightening out the length of tube. The point of separation between the chambers is provided for in a known manner by pressing together the tube length at the V point, but such pressing together cannot provide an effective and reliable-sealing point of separation for mercury which has the capacity to make its way past even the smallest gaps, unless the wall thickness of the tube length is absolutely uniform, which is difficult to accomplish in practice unless production of the tube is made considerably more expensive. Thus the known capsule is not suitable for the storage of the basic materials for dental amalgam in which one material is mercury.

In order to improve the sealing effect at the point of separation, so that no mercury at all can make its way past the point of separation, in accordance with the present invention a capsule of the type specified above has been improved in that the point of separation at the tip of the V-shaped capsule comprises two transverse compression points in which the opposite wall sections of the tube length are pressed against each other, with a section located between the pressure points which is flattened in relation to the original cross-sectional shape of the tube length.

To produce this capsule the invention aims at a method in which an elastic flexible tube length is bent into V-shape with the arms each forming a chamber and with the tip between the arms forming a point of separation between the chambers. The new and characteristic aspect here is that the tube length before bending is pre-shaped into a section at the longitudinal centre of the tube length by providing two transverse points of compression which are mutually separated by an intervening section.

It is preferable if the intervening section of the tube length is flattened during the execution of the compression operations at the same time as the wall section, which should be located on the inside of the V, is being arched around the intended axis of bending.

BRIEF DESCRIPTION OF THE DRAWINGS

To illustrate the present invention this will be described in greater detail in the following by reference to an embodiment and with the aid of the appended drawing in which:

FIG. 1 is a side view of the basic material for the capsule, a length of plastic tubing or plastic hose, FIG. 2 is the side view of an introductory stage during the production of the capsule in accordance with the invention, of the tube length in FIG. 1 consisting in pre-shaping of that section of the tube length which is to form the fold, FIG. 3 is an axial sectional view on a larger scale of the preformed section.

FIG. 4 is a side view of the capsule after filling but before closure

FIG. 5 is a perspective view of the capsule ready for delivery

FIG. 6 is a perspective view of the capsule straightened out so as to mix the components FIG. 7 is a perspective view of the capsule in the state as shown in FIG. 6 together with a holder in which it is to be employed for shaking in a conventional amalgam mixer, and FIG. 8 is a perspective view of the capsule placed in the holder.

DESCRIPTION OF THE PREFERRED EMBODIMENT

The capsule for executing the procedure in accordance with the present invention is made from an elastic bendable tube (hose) of thermoplastic material, preferably polypropene; it is however for example also possible to use polyethylene, polyester or nylon. The tube should preferably be absolutely transparent (glass clear). The thickness of the tube wall should be selected empirically and is dependent on which plastic material is involved; suitable external and internal diameters for a polypropene tube can be 4.9 and 4.1 mm respectively. The tube length should be selected having regard to the quantity of the two components which are to be stored and mixed in the capsule, and to the stroke of the mixer to be used.

Referring to FIGS. 1 to 3 of the drawing, the length of tube is illustrated in FIG. 1 and denoted there by 10 and during the manufacture of the capsule in accordance with the invention this tube length is pre-shaped in a section roughly at the centre as shown in FIG. 2 and 3. Deformation of a section of the tube length at the centre of its length is undertaken by means of a plunger, this giving two points of compression 10 A with a transverse section located between these points of compression 10 B which is flattened in comparison with the original cross-sectional form of the tube length, whereby the wall section on the top side is curved essentially cylindrically around a transverse axis to the tube length, The portion 10B is of the order of 2.5 to 3 mm.

The tube length thus pre-shaped is bent into V-shape as shown in FIG. 4 with the curvature of section 1OB located on the inside, thus providing two arms 11 and 12 which are open at their free ends at 13 and 14 respectively and which are connected with each other at their other ends at the tip of the V 15 which is formed by the pre-formed centre section of the tube length and which has two folds where the indentations 10 A have been made, with the opposite flat wall sections of the length of tube pressed against each other and with the fold separated at the tip of the V by the intervening section 10B. The folds form the point of separation between the two chambers formed by the arms 11 and 12 and thanks to pre-shaping during the provision of the two points of compression 10A this point of separation provides a complete seal between both chambers in the arms even in the case of a component such as mercury which is so difficult to seal.

To ensure that the tube length will retain its V-shape as shown in FIG. 4, means can be provided for holding together the arms 11 and 12 and these means can comprise a strip of tape or string placed around the arms, an enveloping sleeve made of paper, plastic or the like, or a strip of cardboard or plastics with a number of holes in which a V-shaped length of tube as shown in FIG. 4 can be placed in each hole. Also a metal bar or clip can be used. FIG. 5 shows diagrammatically such means by dashed lines 16.

FIG. 4 shows that the V-shaped capsule has been filled with the two components which are to be stored therein. The chamber formed by arm 11 has been filled through the open end 13 with alloy, denoted by 17, whilst the chamber formed by the arm 12 has been provided with a droplet of mercury 18 through the open end 14 of this arm. The amount of alloy and the amount of mercury are obviously proportioned in the manner required for the dental amalgam which is to be formed by mixing the components with each other.

After the capsule has been filled the two arms 11 and 12 are closed at the ends 13 and 14 by a transverse seal 19 and 20, provided by means of heat or ultrasonics. A marking can be provided in each transverse seal to identify the dental amalgam of which the two components are to form part. The appearance of the capsule is now as shown in FIG. 5 and this is the condition in which it should be for storage and distribution of the two components which are kept absolutely separate from each other by means of the effective point of separation at the tip 15. Thus there is no risk at all of the components being mixed as long as the capsule has the V-shape illustrated.

When the amalgam is to be prepared the means 16 which maintain the V-shape are removed and the capsule is straightened out to the shape shown in FIG. 6. This opens up the point of separation formed by the tip 15 so that the alloy 17 and the mercury 18 come into contact with each other and mix in the straightened capsule. It should be noted here that an indentation 21 remains in the tube wall from the previously-formed fold, provided that the plastic material is of such a composition that after straightening of the length of tube there is a certain residual deformation on the part of the tube wall. Inside the capsule the indentation forms a threshold between the chambers formed by arms 11 and 12.

To enable mixing of the alloy and mercury to take place in an amalgam mixer of the conventional type, which is employed with the dental capsules currently available, a holder or adaptor of the type shown in FIG. 7 can be used. This holder contains a channel 22 which is so dimensioned that it can envelop the straightened capsule which can be fed into the trough subject to some elastic deformation on the part of its walls. Since the straightened capsule is subject to some elastic deformation of the walls thereof and can exhibit at the ends of the indentation 21 a couple of slight bulges in the side, the channel 22 has a couple of recesses 22A to provide room for these bulges. The channel 22 is seated on a body 23 the shape of which resembles the dental capsules currently employed.

The holder can be located between the two holder arms, partially indicated by dashed lines at 24 in FIG. 8 on a conventional amalgam mixer of any of the known makes (VIBROMIX, DENTOMAT, SILAMAT, DUOMAT). The capsule inserted in its holder in the amalgam mixer is made to perform a reciprocating movement as shown by the arrow 25 in FIG. 8 or a reciprocating and simultaneously circular motion as shown by the markings 26 in FIG. 8, so that the alloy 17 and the mercury 18 will mix and react with each other during the formation of the amalgam. The threshold formed by the indentation 21 thereby serves to intensify the mixing in the capsule and to prevent the mixture from being compressed, which would make it difficult to remove the amalgam from the capsule. The seals 19 and 20 which by nature are such that they project from the sides of the capsules prevent the capsule from sliding away from the channe1 22 in its lengthwise direction during mixing. As the capsule is completely sealed, there is no risk whatever of mercury in finely divided form escaping from the capsule to the atmosphere at mixing.

When the amalgam has been prepared, the capsule is opened merely by cutting off the length of tube at a suitable position, after which the amalgam can be removed from the capsule for insertion by amalgam gun or conventional plug device.

The embodiment of the invention described indicates that the present invention gives an easily-handled and effective means, also a capsule which is surprisingly simple in the design and functional respects, for storing and mixing basic materials for dental amalgam, by means of which the objectives of the present invention mentioned above can be achieved.

I claim:

1. A capsule for storing and mixing two co-reactive basic materials for a dental amalgam comprising:

two tubular chambers interconnected as an integral structure in a V-shape, the structure being formed from a single elastically bendable length of tubing;

a seal, impenetrable to mercury, between said chambers, said seal including two substantially parallel transverse lines of compression across said length of tubing, the lines of compression comprising the inner ends of said chambers; and a section between said lines of compression, the lateral cross section of said section being open and less than the lateral cross sections of said tubular chambers.

2. The capsule of claim 1 wherein the longitudinal cross section of said section is arch-shaped, the area under the arch being open.

3. A method for storing and mixing two co-reactive materials for dental amalgam comprising the steps of:

applying a pair of parallel transverse pressure lines across one side of an elastically bendable length of tube, the space between said pair of lines forming a separate, unsupported, arched section;

forming a seal, impenetrable to mercury, by bending said bendable length of tube along said pressure lines into a "V" having two arms with said seal therebetween;

placing a droplet of loose mercury into one of said arms and an appropriate alloy in the other arm;

sealing the outer ends of said tube while retaining the arms in the V-shape;

retaining the arms in the V-shape for storage;

releasing the mercury and the alloy for intermixing by straightening out the two arms of the tube from the V shape sufficiently to break the seal; and shaking the tube in a movement having a component of motion along the axial direction of at least one of said arms to intermix said mercury and said alloy.

4. The method of claim 3 wherein said step of releasing leaves bulges on opposite sides of said tube upon said straightening out of the arms and wherein said step of shaking includes utilizing said bulges for preventing the tube from sliding axially while being reciprocated in a conventional amalgam mixer.

5. A method for manufacturing a capsule for storing and mixing two co-reactive basic materials for a dental amalgam comprising:

applying two substantially parallel transverse lines of compression across a length of elastically bendable tubing, said lines of compression being located centrally between the ends of said tubing and forming a section of said tubing between said lines of compression;

bending said length of tubing along said lines of compression with a V-shape, said lines of compression and said section forming a seal impenetrable to mercury, between two chambers open at the ends, said seal being breakable by the relative straightening of the chambers into a straight line, and sealing said open ends after the two co-reactive materials have been received in the chambers.

6. The method of claim 5 wherein the substep of forming a section of said tubing includes reducing the area of the lateral cross section of the section to less than the area of the lateral cross section of said chambers and arching the longitudinal cross section of the section between the lines of compression.

* * * * *